(12) United States Patent
Oishi

(10) Patent No.: US 8,814,794 B2
(45) Date of Patent: Aug. 26, 2014

(54) MEASURING SYSTEM, IMAGE FORMING METHOD, AND PROGRAM

(75) Inventor: Takuji Oishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 882 days.

(21) Appl. No.: 12/964,654

(22) Filed: Dec. 9, 2010

(65) Prior Publication Data

US 2011/0149680 A1 Jun. 23, 2011

(30) Foreign Application Priority Data

Dec. 17, 2009 (JP) ................ 2009-071062

(51) Int. Cl.
*A61B 8/00* (2006.01)
(52) U.S. Cl.
USPC .......................................... 600/437; 600/443
(58) Field of Classification Search
USPC ................................................ 600/437–480
See application file for complete search history.

(56) References Cited

U.S. PATENT DOCUMENTS 5,840,023 A 11/1998 Oraevsky et al.

FOREIGN PATENT DOCUMENTS

JP 2001-507952 A 6/2001
WO WO9814118 A1 4/1998

*Primary Examiner* — Unsu Jung
*Assistant Examiner* — Shahdeep Mohammed
(74) *Attorney, Agent, or Firm* — Canon USA Inc. IP Division

(57) ABSTRACT

A measuring system for receiving acoustic waves and producing image data includes an acoustic wave receiver that detects acoustic waves which are generated by irradiating a specimen with pulsed light. The acoustic wave receiver converts the detected acoustic waves into an electric signal, and an image forming apparatus generates image data by using the electric signal. An artifact attributable to a band of an acoustic wave receiver is distinguished and reduced based on the positional relationship among respective voxel data representing an actual image and a reflected image of a light absorber located within the specimen and related artifacts, as viewed on the image data, by utilizing an acoustic wave reflecting surface on which the specimen is disposed.

11 Claims, 9 Drawing Sheets

MEASURING SYSTEM, IMAGE FORMING METHOD, AND PROGRAM

TECHNICAL FIELD

The present invention relates to a measuring system for receiving acoustic waves and producing image data, an image forming method for producing image data from acoustic waves, and a program for causing the image forming method to be executed.

BACKGROUND ART

Studies of an optical imaging apparatus for causing light irradiated to a specimen from a light source, such as a laser, to propagate inside the specimen and for obtaining information regarding the interior of the specimen have been positively progressed primarily in the medial field. As one of optical imaging techniques based on those studies, Photoacoustic Tomography (PAT) has been proposed. See, for example, U.S. Pat. No. 5,840,023 entitled "Optoacoustic Imaging for Medical Diagnosis" (hereafter referred to as "Patent Literature 1").

In the Photoacoustic Tomography technique, pulsed light is first generated from a light source and irradiated to a specimen. The irradiated light is caused to propagate and diffuse inside the specimen, while body tissues absorb energy of the light and generate acoustic waves (typically ultrasonic waves) from the same. The generated acoustic waves are detected at plural points located in surrounding relation to the specimen, and obtained signals are mathematically analyzed and processed into image data. Such processing is referred to as imaging hereinafter. An initial pressure generation distribution or an optical characteristic value distribution, particularly, a light-energy absorption density distribution, inside the specimen can be obtained with the imaging, and information regarding the interior of the specimen, such as the position of a malignant tumor, can be obtained.

CITATION LIST

Patent Literature

PTL 1 U.S. Pat. No. 5,840,023

An artifact may appear sometimes in an image obtained with the imaging. The artifact implies an image that appears as if something exists there, although it actually does not exist. The artifact is also called a ghost. In particular, the artifact attributable to a band of an acoustic wave receiver appears noticeably when a view angle is restrictive, e.g., when a position at which an acoustic wave signal is obtained is located on a plane in a certain direction instead of spanning over 360 degrees around the specimen. Hitherto, the artifact has been indistinguishable from an image of an actually-existing light absorber (i.e., from an actual image).

Therefore, an object of the present invention is to distinguish or reduce (suppress) an artifact attributable to a band of an acoustic wave receiver.

SUMMARY OF INVENTION

According to the present invention, there is provided a measuring system comprising an acoustic wave receiver for receiving acoustic waves which are generated by irradiating light into a specimen, and for converting the received acoustic waves to an electrical signal, and an image forming apparatus for producing image data by using the electrical signal, wherein the acoustic wave receiver receives at least direct waves in acoustic waves generated from a detection target inside the specimen, which directly reach the acoustic wave receiver, and reflected waves in the acoustic waves generated from the detection target, which have been reflected by an acoustic wave reflecting surface disposed in the specimen, and converts the received waves to respective electrical signals, the image forming apparatus comprising a data producing unit for converting the electrical signal converted from the direct waves and the electrical signal converted from the reflected waves to voxel data or pixel data, thereby producing image data, a determining unit for determining whether, as viewed on the image data, a position of the voxel data or the pixel data converted from the direct waves and a position of the voxel data or the pixel data converted from the reflected waves are symmetrical with respect to a position corresponding to the acoustic wave reflecting surface on the image data, and a processing unit for executing processing to distinguish or reduce images of the voxel data or the pixel data, which are determined to be not symmetrical by the determining unit.

Further, according to the present invention, there is provided a measuring system comprising an acoustic wave receiver for receiving acoustic waves which are generated by irradiating light to a specimen, and for converting the received acoustic waves to an electrical signal, and an image forming apparatus for producing image data by using the electrical signal, wherein the acoustic wave receiver receives at least direct waves in acoustic waves generated from a detection target inside the specimen, which directly reach the acoustic wave receiver, and reflected waves in the acoustic waves generated from the detection target, which have been reflected by an acoustic wave reflecting surface disposed in the specimen, and converts the received waves to respective electrical signals, the image forming apparatus comprising a data producing unit for converting the electrical signal converted from the direct waves and the electrical signal converted from the reflected waves to voxel data or pixel data, thereby producing image data, a folded-data producing unit for folding the image data at a position corresponding to the acoustic wave reflecting surface on the image data, thereby producing folded data, and a superimposing unit for superimposing the folded data with the image data before being folded.

Further features of the present invention will become apparent from the following description of exemplary embodiments with reference to the attached drawings.

DESCRIPTION OF EMBODIMENTS

The present invention will be described in detail below with reference to the drawings. Be it noted that, in the present invention, acoustic waves imply elastic waves which include the so-called sound waves, ultrasonic waves, and photoacoustic waves, and which are generated inside a specimen when light (electromagnetic waves), such as a near infrared ray, is irradiated to the specimen.

Embodiment 1

Figure 1:
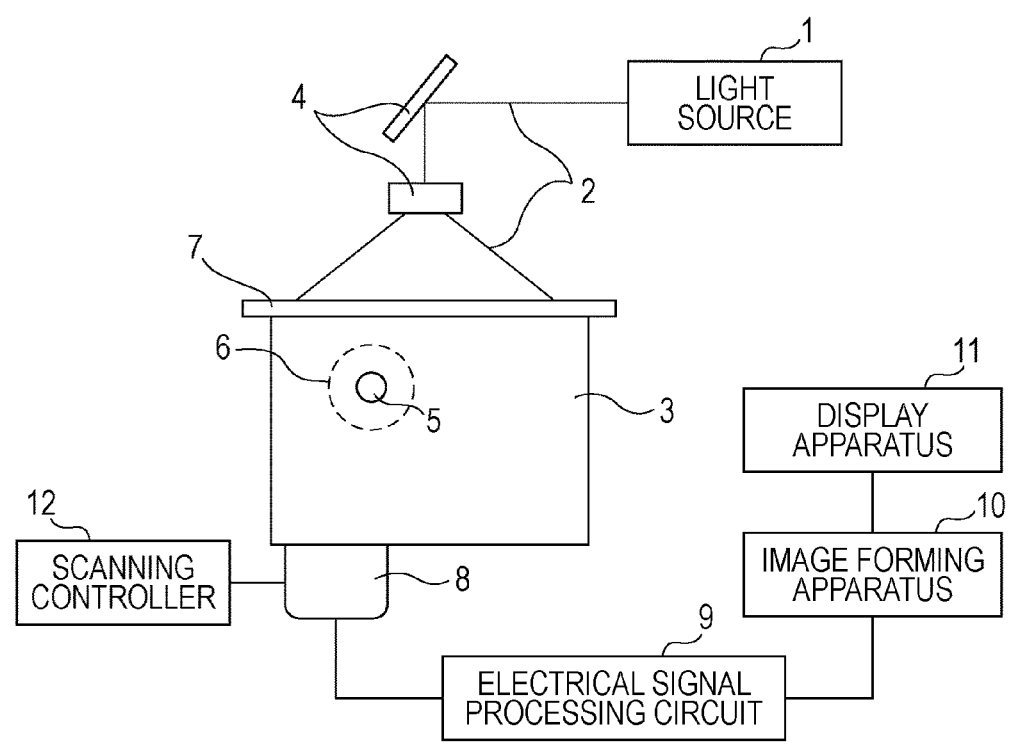
FIG. 1 is a block diagram illustrating one example of configuration of a measuring system to which the present invention can be applied.

Embodiment 1 of the present invention is described while referring to the drawings. A system configuration for specifying, distinguishing or reducing (including the case of removing) an artifact is described in this embodiment. FIG. 1 is a block diagram of a measuring system to which the present invention can be applied. In the measuring system utilizing the Photoacoustic Tomography technique, light 2 (pulsed light) is generated from a light source 1. The light 2 is irradiated onto a specimen 3 through optical devices 4 (optical system), such as a lens and a mirror. A light absorber 5 (i.e., an object or target to be detected) inside the specimen 3 absorbs energy of the light and generates acoustic waves 6. One part of the generated acoustic waves 6 directly reaches an acoustic wave receiver 8, and the other part of the generated acoustic waves first reflects on an acoustic wave reflecting plate 7 and then reaches the acoustic wave receiver 8 after being reflected by the acoustic wave reflecting plate 7 that serves as an acoustic wave reflecting surface. In the following description, the acoustic waves directly reaching the acoustic wave receiver 8 without being reflected are referred to as "direct waves", and the acoustic waves reaching the acoustic wave receiver 8 after being reflected by the acoustic wave reflecting plate 7 are referred to as "reflected waves". Accordingly, the acoustic wave receiver 8 detects the direct waves earlier (first) than the reflected waves (second). The acoustic wave receiver 8 receives the acoustic waves (direct waves and reflected waves) and converts the received waves into an electrical signal. The electrical signal is then output to an electrical signal processing circuit 9. More specifically, the acoustic wave receiver 8 is configured to perform measurements at various locations of the specimen 3; and to that end, the acoustic wave receiver 8 is mechanically moved (scanned) with respect to the specimen 3 by a scanning controller 12. The electrical signal processing circuit 9 receives the electrical signal output from the acoustic wave receiver 8, executes filtering, amplification, digital conversion, etc. of the electrical signal and outputs an electrical signal after the digital conversion (i.e., a digital signal) to an image forming apparatus 10. The image forming apparatus 10 produces image data by using the digital signal; and the produced image data is displayed as an image by a display apparatus 11. In addition to being displayed, the produced image data may be stored in a non-illustrated memory unit (data storage device), or it may be transmitted to a remote location for image processing.

In the present invention, the acoustic wave reflecting plate 7 serving as the acoustic wave reflecting surface is disposed on the specimen 3. Preferably, the acoustic wave reflecting plate 7 has a flat surface on its side facing the specimen 3 and has acoustic impedance (e.g., about $3 \times 10^6$ Kg/m$^2$·s) that is substantially different from the acoustic impedance of the specimen 3. Further, the acoustic wave reflecting plate 7 is preferably made of a material, which is transparent to the light 2 and which allows the light 2 to sufficiently pass through the same. This is because such a material enables the light to be irradiated to the specimen from the side where the acoustic wave reflecting plate 7 is disposed. When pressing plates are disposed for pressing the specimen from both the sides, the pressing plate disposed on the side opposite to the acoustic wave receiver 8 may be used as an acoustic wave reflecting plate, or the acoustic wave reflecting surface may be disposed on the pressing plate. Alternatively, the pressing plate itself may serve as the acoustic wave reflecting surface. In other words, the acoustic wave reflecting surface may be the surface on which the specimen is disposed.

The light source 1 is intended to irradiate light of a particular wavelength, which is absorbable by a particular component (e.g., hemoglobin) among the components of a living body. As the light source 1, the measuring system includes at least one pulsed light source capable of generating pulsed light. For example, light pulses with a duration of 5 nanoseconds to 50 nanoseconds may be suitable for examining certain specimens, while shorter pulses (in the range of femtoseconds) or larger pulses (in a range of hundreds of nanoseconds) may be desirable for other specimens. Although a laser having a high intensity output is preferably used as the light source 1, a light emitting diode or the like can also be used instead of the laser. Suitable one of various lasers, such as a solid laser, a gas laser, a dye laser, and a semiconductor laser, can be used as the laser. The light 2 may be irradiated from the side where the acoustic wave receiver 8 is disposed, or it may be irradiated from the side opposite to the acoustic wave receiver 8. Alternatively, the light may be irradiated from both the sides of the specimen.

The optical devices 4 may include without limitation, for example, a mirror for reflecting light, and a lens for condensing or spreading light to change the shape of a light beam. In addition to the mirror and the lens, an optical waveguide, an optical fiber, etc. can also be used as optical components. The optical component may be of any type so long as it enables the light 2 emitted from the light source 1 to be irradiated in the desired form to the specimen 3. The light 2 is preferably diverged by the lens to be spread into a certain area sufficient to irradiate a region of interest in the specimen 3. Further, a zone where the light 2 is irradiated onto the specimen 3 is preferably movable with respect to the specimen. In other words, the measuring system is preferably constituted such that the light generated from the light source 1 is movable over the specimen. Such mobility of the light enables the light to be irradiated over a larger range. More preferably, the zone where the light 2 is irradiated to the specimen 3 (i.e., the light irradiated to the specimen) is moved in synchronism with the acoustic wave receiver 8. A method of moving the zone where the light is irradiated onto the specimen can be practiced, for example, by a manner using, e.g., a movable mirror, or by a manner of mechanically moving the light source itself. Alternatively, the zone where the light is irradiated to the specimen and the acoustic wave receiver 8 may be stationary, while the specimen itself moves.

The acoustic wave receiver 8 includes one or more devices each of which receives acoustic waves and converts the acoustic waves to an electrical signal. In one embodiment, the acoustic wave receiver 8 is constituted by, e.g., a transducer utilizing a piezoelectric phenomenon, a transducer utilizing optical resonance, or a transducer utilizing change of capacitance. The acoustic wave receiver 8 is of any type as long as it can receive acoustic waves and can convert the acoustic waves to an electrical signal. By one- or two-dimensionally arranging the device for receiving the acoustic waves in plural locations, it is possible to simultaneously receive (detect) the acoustic waves at plural places, to shorten a reception time, and to reduce an influence of vibration of the specimen, etc. Alternatively, similar signals to those obtained by two- or one-dimensionally arranging the devices can also be obtained by scanning one device. A plurality of devices may be disposed over an entire surface of the specimen. In addition, an acoustic matching material, such as a gel for achieving acoustic matching, is preferably applied between the acoustic wave receiver 8 and the specimen.

Next, image data obtained in the image forming apparatus 10 through an analysis process will be described in detail by referring to FIG. 2. The image data implies data representing information regarding the interior of the specimen regardless of whether the information is two- or three-dimensional. The two-dimensional information is constituted by arraying a plurality of pixel data, and the three-dimensional information is constituted by arraying a plurality of voxel data. As used herein, a "voxel" is a unit of graphic information that defines the smallest volume element in three-dimensional space. In other words, voxel is the 3D analogue of a pixel, the latter representing the smallest area of a two dimensional image. The pixel data and the voxel data are obtained by executing an analysis process on the acoustic signals, which are obtained at plural positions, by using an image data producing method (image reconstructing method) based on, e.g., a time-domain or Fourier-domain process. While three-dimensional image data is described in the following, the present invention can be applied to two-dimensional image data as well.

Figure 2:
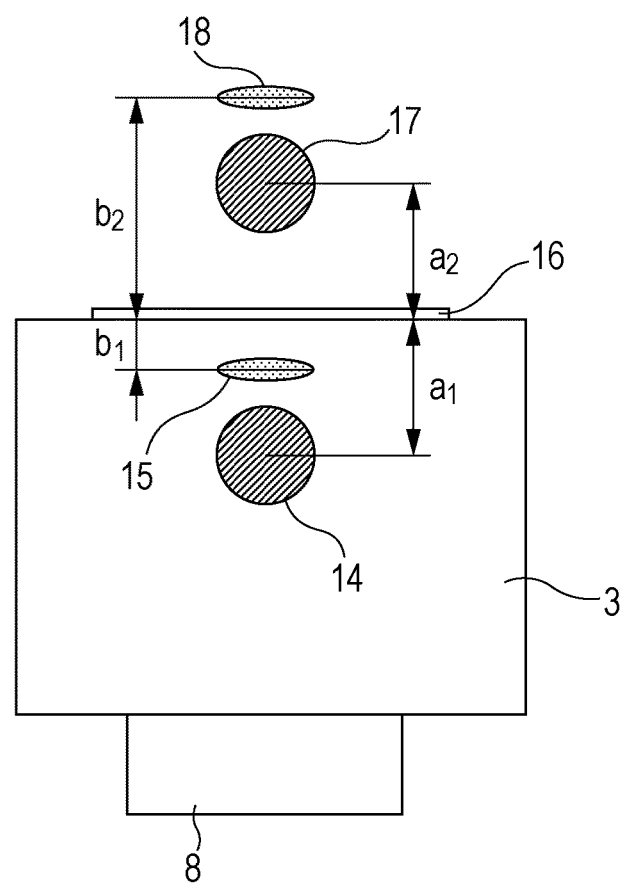
FIG. 2 is a schematic view to explain one example of the positional relationship among an actual image, a reflected image, and their artifacts all obtained in the measuring system to which the present invention can be applied.

FIG. 2 illustrates a conceptual view comparing the positional relationship between images, which are represented by the obtained image data, with respective positions of the specimen and the acoustic wave receiver. The acoustic waves excited by the light spread in the spherical form from a light absorber, i.e., a position from which the acoustic waves are generated. One part of the acoustic waves directly reaches, as the direct waves, to the acoustic wave receiver 8. The other part of the acoustic waves is reflected by an acoustic wave reflecting surface 16 (provided by the acoustic wave reflecting plate 7) having different acoustic impedance and the reflected waves reach the acoustic wave receiver 8 at a later time than the direct waves. The acoustic wave receiver 8 receives both the direct waves and the reflected waves and converts them to respective electrical signals. Voxel data providing an actual image 14 of the light absorber and voxel data providing a reflected image 17 thereof are obtained by executing the analysis process of the electrical signals including those of both the direct waves and the reflected waves. The actual image 14 is an image formed by the direct waves, and the reflected image 17 is an image formed by the reflected waves. The reflected image 17 appears at a position in accordance with the physical law regarding reflection. Such a position can be calculated if the shape and the position of the acoustic wave reflecting surface 16 are known. When the acoustic wave reflecting surface 16 is a flat surface, the relationship between the actual image 14 and the reflected image 17 are the same as that between an actual image and a reflected image seen in a mirror. More specifically, in FIG. 2, the position where the reflected image 17 appears is defined as a position away from the actual image 14 in a direction normal to the acoustic wave reflecting surface 16 through the same distance as that from the acoustic wave reflecting surface 16 to the actual image 14, i.e., a position where $a_1=a_2$ is held. Further, because an artifact is attributable to the band of the acoustic wave receiver, there appear not only an artifact 15 originating from the actual image 14, but also an artifact 18 originating from the reflected image 17 in a similar way.

A description is now made about a generation mechanism of the artifact, which is attributable to the band of the acoustic wave receiver and which is a problem to be addressed by the present invention. In the Photoacoustic Tomography, it is known that acoustic waves excited by light are made up of frequency components spanning over a wide band. Generally, because an acoustic wave receiver for receiving those acoustic waves is able to receive only a part of the band, an electrical signal output from the acoustic wave receiver takes a signal waveform constituted only by the partial frequency band. At that time, due to lack of the band, the signal overshoots beyond a baseline when it returns to the baseline, thus generating ringing (vibration). Such a ringing component generated is attributable to the band of the acoustic wave receiver and causes an artifact to be present in the detected image. The reason for the creation of such an artifact is believed to reside in that the structure of the specimen is basically reproduced by only signal components from a light absorber mutually intensifying with each other, but if the ringing occurs, the ringing components also mutually intensify with each other, thus causing the artifact to appear.

The signal vibration (ringing component) causing the artifact appears at a position later than the genuine signal in terms of time, looking from the acoustic wave receiver. Accordingly, when the electrical signal is converted to volume data through the analysis process, the artifact always appears at a position farther away from the acoustic wave receiver 8 than each of the actual image and the reflected image, as illustrated in FIG. 2. In other words, the relationship between a distance $b_1$ from the artifact 15 originating from the actual image to the acoustic wave reflecting surface 16 and a distance $b_2$ from the reflected image 18 to the acoustic wave reflecting surface 16 is given by $b_1 \neq b_2$. Thus, when comparing those images on both the sides of the acoustic wave reflecting surface 16 as a boundary, the images of the actually existing light absorber appear at positions which are plane-symmetric, and the artifacts appear at positions which are not plane-symmetric (i.e., plane-asymmetric) with respect to the acoustic wave reflecting surface 16.

Figure 3:
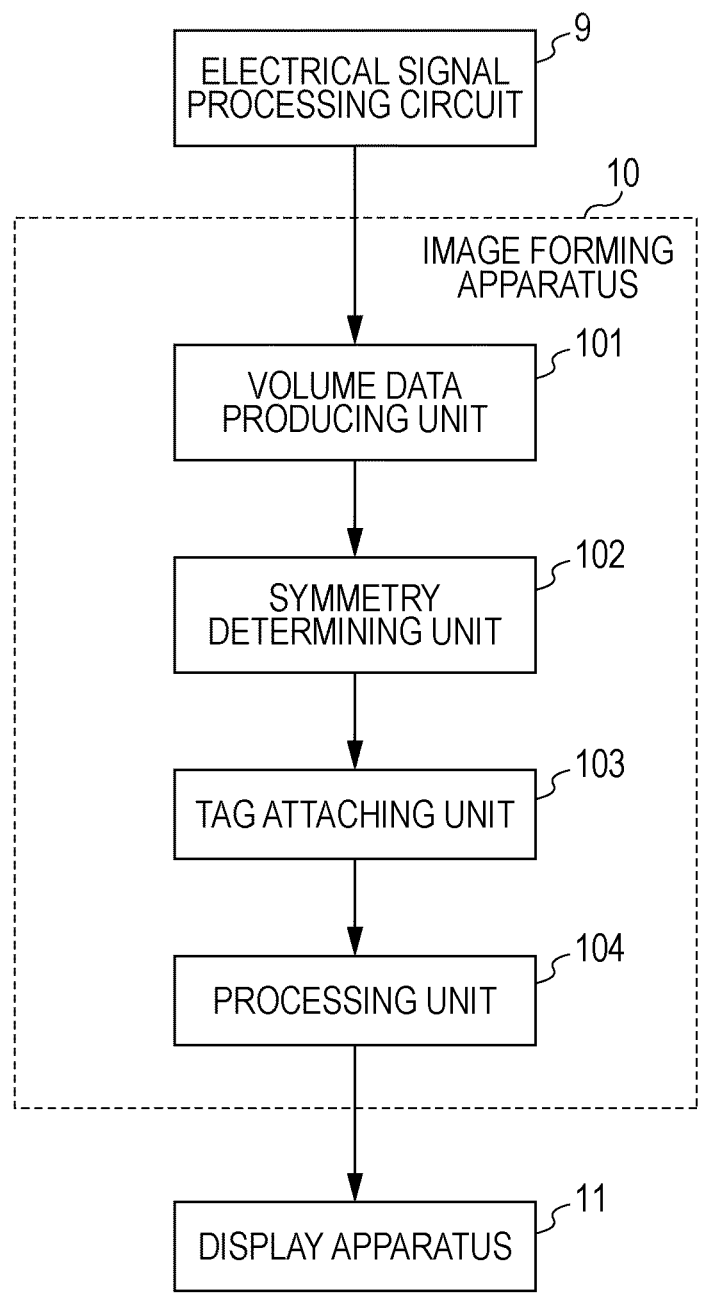
FIG. 3 is a block diagram illustrating one example of internal configuration of an image forming apparatus according to Embodiment 1 of the present invention.
Figure 4:
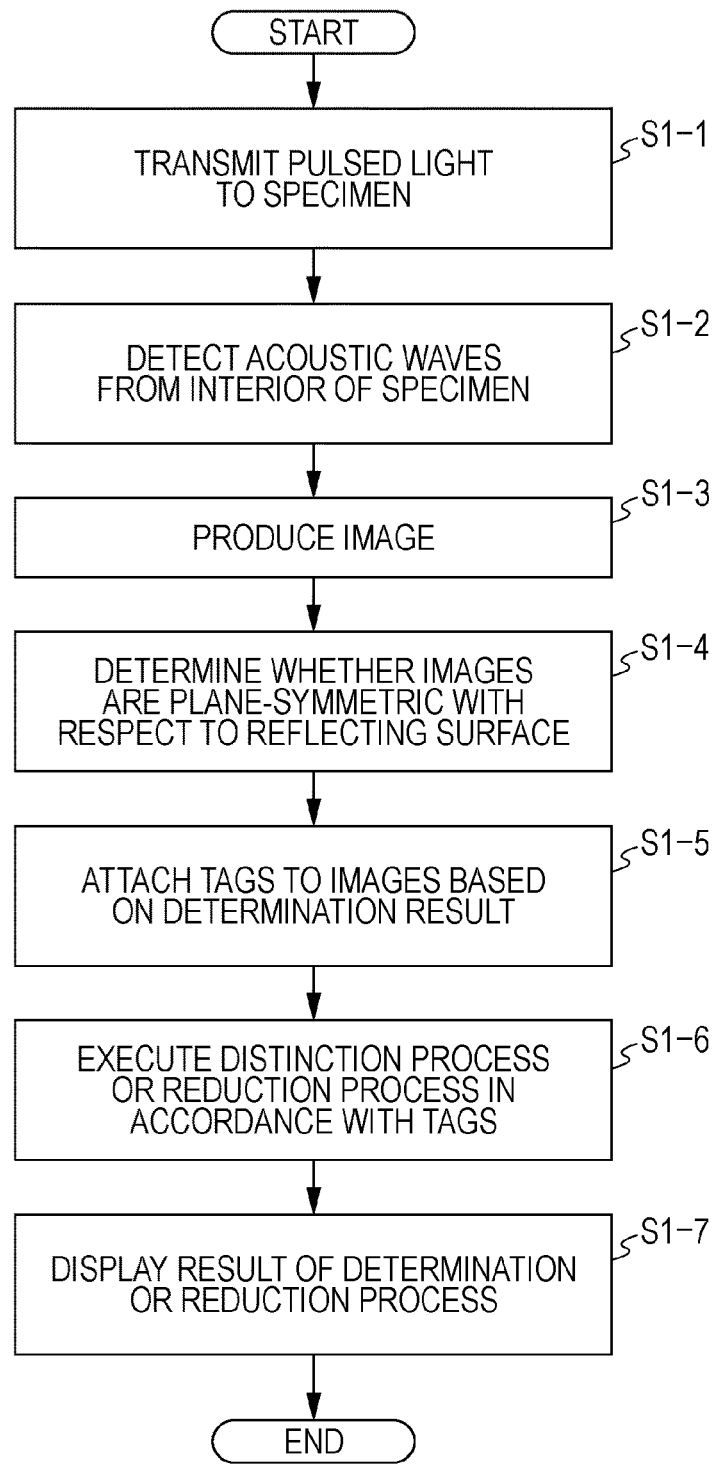
FIG. 4 illustrates a processing flow in Embodiment 1 of the present invention.

Next, a method, to which the present invention can be applied, for specifying and distinguishing or reducing the artifact is described by referring to FIGS. 3 and 4. FIG. 3 is a block diagram illustrating internal configuration of the image forming apparatus according to Embodiment 1, and FIG. 4 is a flowchart of processing to distinguish the artifact.

First, the pulsed light is irradiated to the specimen (S1-1), and acoustic waves excited by the pulsed light are received by the acoustic wave receiver (S1-2). An electrical signal output from the acoustic wave receiver is amplified and subjected to analog-digital conversion in the electrical signal processing circuit 9, and then stored as a digital signal. In those steps, the acoustic wave receiver is held in a receivable state at least during a period from the irradiation of the light to the specimen until arrival of the reflected waves to the acoustic wave receiver. Further, the electrical signal processing circuit 9 is required to store, as the digital signal, the acoustic waves that have been received during such a period. Stated another way, the electrical signal processing circuit 9 stores at least respective digital signals of the direct waves and the reflected waves. In addition, the digital signals stored in the electrical signal processing circuit 9 are obtained at plural positions inside the specimen. A volume data producing unit 101 in the image forming apparatus 10 converts the digital signals obtained at the plural positions to respective voxel data representing spatial information inside the specimen, thereby producing image data (S1-3).

Then, in a symmetry determining unit 102, it is determined (S1-4) whether, as viewed on the produced image data, the positions of the voxel data representing the appeared images are plane-symmetrical with respect to a position corresponding to the acoustic wave reflecting surface. Here, because the distance from the acoustic wave reflecting surface to the acoustic wave receiver is known, the position corresponding to the acoustic wave reflecting surface, as viewed on the produced image data, is also known. Accordingly, it is possible to determine whether the positions of the voxel data representing the appeared images are plane-symmetrical with respect to the position corresponding to the acoustic wave reflecting surface as viewed on the produced image data. Another conceivable method is to utilize acoustic waves generated at the acoustic wave reflecting surface. In many cases, the specimen 3 and the acoustic wave reflecting plate 7 differ in light absorption characteristics from each other, and acoustic waves are generated at an interface (acoustic wave reflecting surface) between the specimen and the acoustic wave reflecting plate. An image based on the acoustic waves having generated at the acoustic wave reflecting surface (hereinafter referred to as an "image of the acoustic wave reflecting surface") is formed by receiving the acoustic waves having generated at the acoustic wave reflecting surface and converting the received acoustic waves to voxel data. By using, as a reference, the position of the voxel data representing the image of the acoustic wave reflecting surface (i.e., the voxel data based on the acoustic waves having generated at the acoustic wave reflecting surface), therefore, whether the other images are plane-symmetrical or not may be determined. Through the steps described above, when the appeared images are not plane-symmetrical, they can be specified as the artifacts.

A tag attaching unit 103 attaches tags to the voxel data representing the images (S1-5) that are not plane-symmetrical and which are specified as the artifacts.

Next, a processing unit 104 executes a distinction process (S1-6) on the voxel data representing the images attached with the tags, i.e., the tagged voxel data representing the images which are not plane-symmetrical and which are specified as the artifacts, by using a coloring technique, for example, such that the relevant images can be distinguished as the artifacts when they are displayed on the display apparatus 11. In addition to the distinction process such as simple coloring, a reduction (suppression) process may be executed so as to display the voxel data having been specified as the artifacts in a relatively light color, or to indicate those voxel data in a color corresponding to a background level so that the voxel data representing artifacts are not displayed as distinct images. Further, in addition to the distinction process, the tagged voxel data representing the artifacts may be replaced by other voxel data, such as by voxel data surrounding the tagged voxel data or by voxel data plane-symmetrical to the tagged voxel data, thereby effectively suppressing (removing) the artifacts.

Finally, the display apparatus 11 displays, for example, a sectional image or a 3D-rendering image, of the voxel data (S1-7). Through the steps described above, the artifacts can be specified and distinguished or reduced.

Embodiment 2

While the artifacts are specified and distinguished or reduced in Embodiment 1, Embodiment 2 is described in connection with a system configuration for reducing the artifacts without specifying them in image data.

Figure 5:
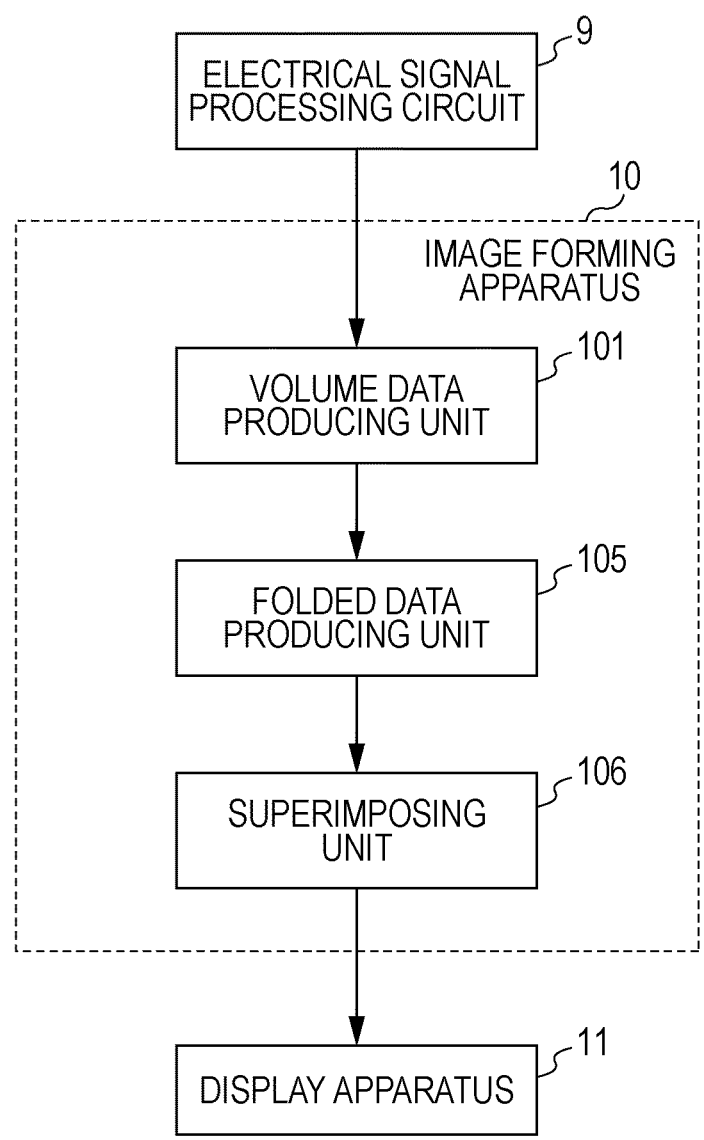
FIG. 5 is a block diagram illustrating one example of internal configuration of an image forming apparatus according to Embodiment 2 of the present invention.
Figure 6:
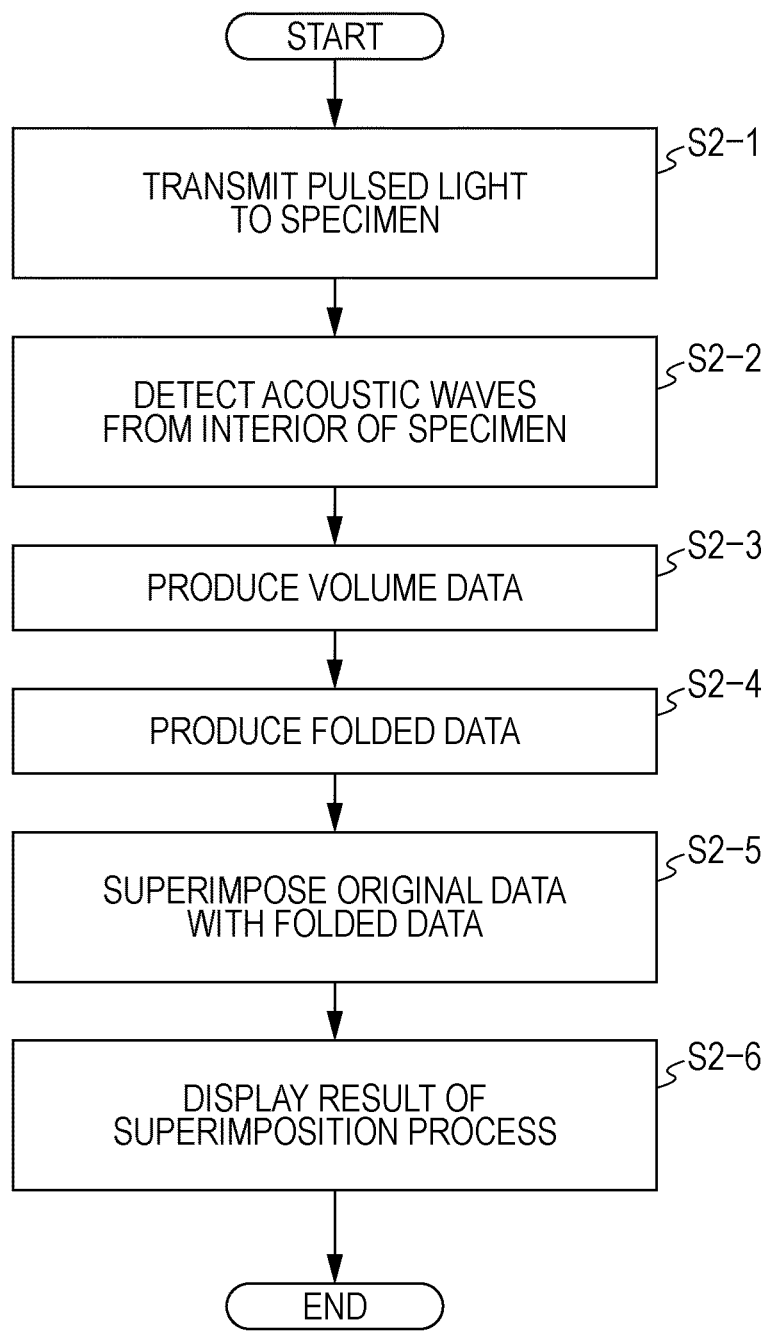
FIG. 6 illustrates a processing flow in Embodiment 2 of the present invention.

FIG. 5 is a block diagram illustrating internal configuration of an image forming apparatus according to Embodiment 2, and FIG. 6 is a flowchart of processing to reduce the artifacts. In Embodiment 2, steps until the image data is produced are the same as those in Embodiment 1. Stated another way, processing up to S2-3 in which the volume data producing unit 101 produces the image data is the same as the processing up to S1-3 in Embodiment 1.

Next, a folded-data producing unit 105 folds the voxel data of the produced image data, which correspond to the side farther away from the acoustic wave reflecting surface when viewed from the acoustic wave detector, i.e., the voxel data in a region where the voxel data providing the reflected image are present, thereby producing folded data (S2-4).

Further, a superimposing unit 106 executes a process of superimposing the folded data with the original image data (S2-5). In image data after being subjected to the superimposition process, the voxel data representing the actual image formed by the actually existing light absorber is additively superimposed with the voxel data representing the reflected image, whereby signals of both the voxel data mutually intensify with each other. However, the respective voxel data of the artifacts are not additively superimposed, the intensity of a resulting signal is relatively weak. Assuming that a voxel value (intensity) of the original image data at a position of x, y and z is $A_1(x, y, z)$ and a voxel value (intensity) of the folded data at the position of x, y and z is $A_2(x, y, z)$, a concrete superimposition process is executed by using the following formula (1):

$$\sqrt{A_1(x,y,z) \times A_2(x,y,z)} \quad (1)$$

The superimposition process is executed on all voxels. Even when the superimposition process is executed by simple multiplication, the artifacts can be reduced. However, the voxel value (intensity) of the actual image is squared by the multiplication. Therefore, the root of the squared value is preferably taken in order to keep a quantitative characteristic, i.e., linearity, of the voxel value. With the superimposition process, the artifacts are reduced when there is a background. When there is no background, the artifacts can be removed because the artifacts are multiplied by zero. Thus, the lower the background, the greater is an effect of reducing the artifacts. In addition, the superimposition process may be executed in other various manners, such as a manner based on the following formula (2):

$$A_1(x,y,z) + A_2(x,y,z) \quad (2)$$

Finally, data obtained with the superimposition process is displayed as, for example, a sectional image or a 3D-rendering image, by the display apparatus 11 (S2-6).

Through the steps described above, the artifacts can be reduced without the step of specifying the artifacts.

Embodiment 3

Embodiment 3 is described in connection with the case where the acoustic wave reflecting plate 7 in FIG. 1 has a curved surface. In this embodiment, image data is produced in a similar manner to that in Embodiments 1 and 2. However, when the acoustic wave reflecting plate has a curved surface, a resulting reflected image is distorted in accordance with the shape of the curved surface. In view of the above point, the distortion caused in the reflected image is calculated from the shape of the reflected interface, and coordinate transform of the position of the voxel data representing the relevant reflected image is executed as if the acoustic waves are reflected by a flat reflecting plate. In other words, the position of the voxel data representing the reflected image is coordinate-transformed to the position of voxel data that is to be obtained when the acoustic wave reflecting surface is a flat surface. When the caused distortion is known in advance, a formula or a table for executing the coordinate transform may be prepared, and the prepared formula or table may be applied to each voxel data.

Thereafter, the artifacts can be distinguished and reduced in a similar manner to that in Embodiment 1 and Embodiment 2.

Embodiment 4

Embodiment 4 is described in connection with the case where the acoustic wave reflecting plate providing the acoustic wave reflecting surface is not physically present. By extending the method used in Embodiment 3 to be adapted for the reflecting plate having the curved surface, the present invention can be further applied to the case where there is no reflecting plate. When the specimen is in air and the acoustic impedance of the specimen differs from that of air, acoustic waves are reflected at the interface between the specimen and the air. The shape of the interface between the specimen and the air is read by a 3D scanning apparatus, and coordinate transform of the position of the voxel data representing the relevant reflected image is executed as if the acoustic waves are reflected by a flat reflecting plate, while considering, from the read shape of the interface, the distortion caused in the reflected image as in Embodiment 3. Further, because acoustic waves are generated at the interface between the specimen and the air (i.e., at the acoustic wave reflecting surface), voxel data of the acoustic waves generated at the interface between the specimen and the air may be itself utilized. Stated another way, by utilizing the position of the voxel data of the acoustic waves generated at the interface, the caused distortion can be examined without reading the shape of the interface by the 3D scanning apparatus.

Thereafter, the artifacts can be distinguished or reduced in a similar manner to that in Embodiment 1 and Embodiment 2.

In addition, the present invention can also be implemented by executing the following process. More specifically, software (program) for implementing the functions of Embodiments 1 to 4 described above is supplied to a system or an apparatus via a network or a known type of storage media, and to a computer (or a CPU, an MPU, etc.) in the system, so that the apparatus reads and executes the program.

EXAMPLE

Results of experiments carried out to confirm the advantageous effect of at least one embodiment (e.g., Embodiment 2) of the present invention are described. Details of an experimental system are as follows. A base material of a specimen was a mixture of soy-oil injection Intralipid and water. The mixture was shaped into a rectangular parallelepiped by using agar. A light absorber prepared by mixing soy-oil injection Intralipid, water, and a black writing fluid (India ink) and shaping the mixture into a sphere was placed inside the specimen. The specimen was put in air. The specimen was irradiated with pulsed light having pulses on the order of a few hundred nanoseconds, and having a wavelength of 1064 nm. The pulsed light was repeatedly irradiated onto the specimen from one side by using a Nd:YAG laser in such a manner that the light was spread so as to impinge upon an entire surface of the specimen. An acoustic wave transmission plate made of a methylpentene polymer was held in contact with a surface of the specimen on the side opposed to the incident surface thereof to which the pulsed light was irradiated. A 2D-array acoustic wave receiver was installed with the acoustic wave transmission plate interposed between the specimen and the 2D-array acoustic wave receiver. An acoustic matching gel was applied to each of the interface between the specimen and the acoustic wave transmission plate and the interface between the acoustic wave transmission plate and the acoustic wave receiver. The 2D-array acoustic wave receiver used in the experimental example was made of a total 324 of devices, i.e., 18 devices in the X direction and 18 devices in the Y direction, which were arrayed at a pitch of 2 mm in each of the X and Y directions. Each of those devices had a frequency band of 1 MHz±40%. In this EXAMPLE, a separate acoustic wave reflecting plate was not used, but the pulsed light incident surface was treated as the acoustic wave reflecting surface because the pulsed light incident surface was held in contact with air having different acoustic impedance.

Figure 7:
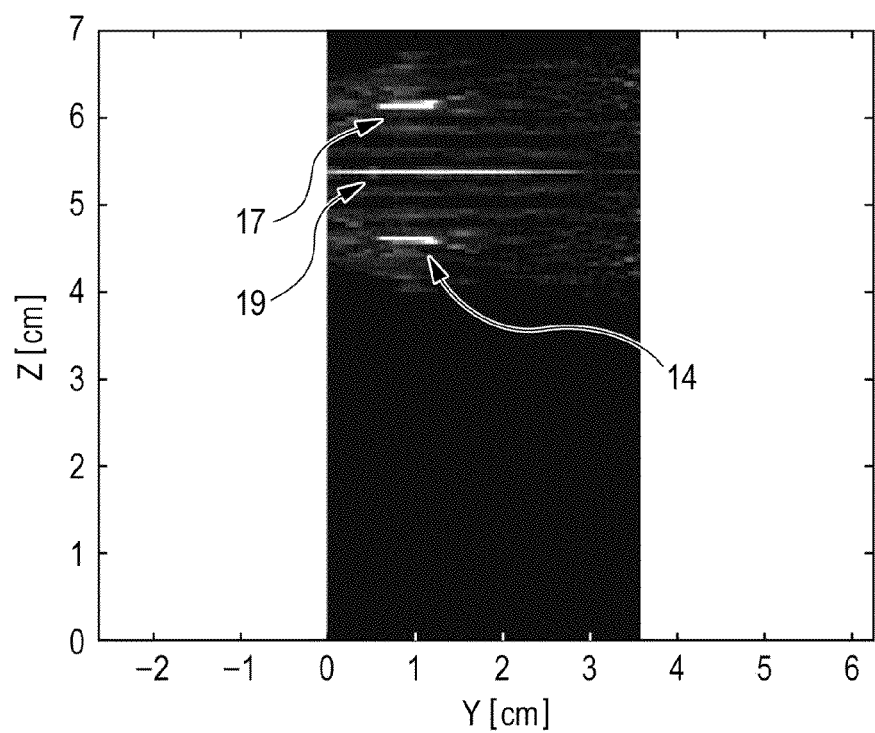
FIG. 7 illustrates a result obtained with EXAMPLE when the present invention is applied.
Figure 8:
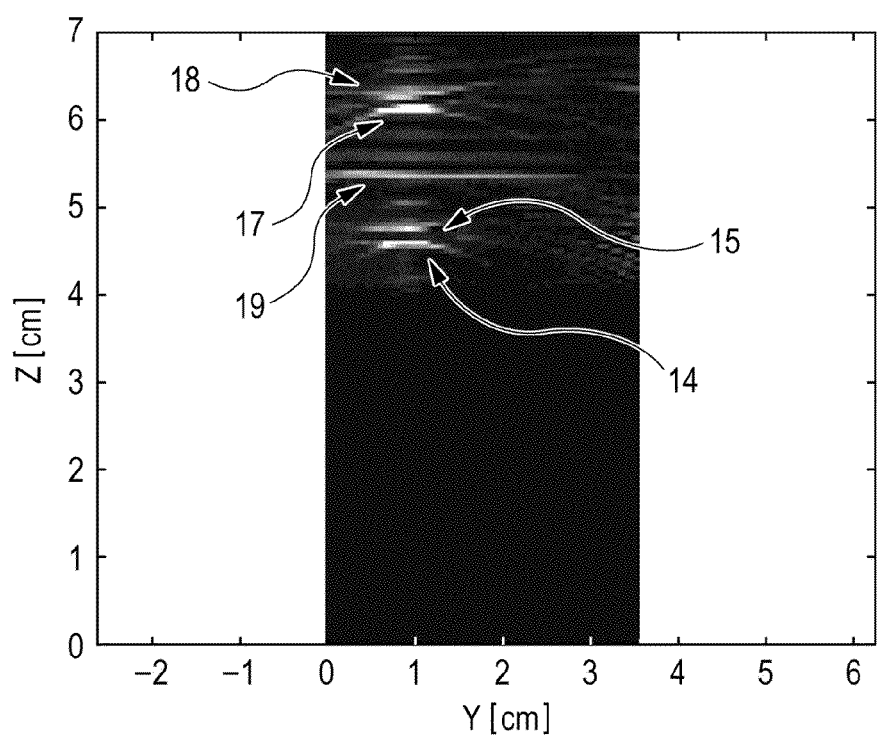
FIG. 8 illustrates a result obtained by using an image data producing method based on known techniques.

FIG. 7 illustrates an MIP (Maximum Intensity Projection) result obtained by employing Embodiment 2 of the present invention. The superimposing method used here is based on the formula (1). Further, FIG. 8 illustrates, as COMPARATIVE EXAMPLE, an MIP result of image data obtained with the known image data producing method, to which the present invention is not applied, by using the same experiment system as that described above. In each of FIGS. 7 and 8, the horizontal axis indicates a distance in the Y direction, and the vertical axis indicates a distance in the Z direction. A line appearing near Z=4.5 cm is an actual image 14 of the light absorber, a line appearing near Z=5.4 cm is an image 19 of the acoustic wave reflecting surface, and a line appearing near Z=6.1 cm is a reflected image 17 of the light absorber. Further, in FIG. 8, a line appearing near Z=4.7 cm is an artifact 15 of the actual image, and a line appearing near Z=6.3 cm is an artifact 18 of the reflected image.

As seen from FIG. 7, the artifacts are reduced in comparison with those in FIG. 8.

Figure 9:
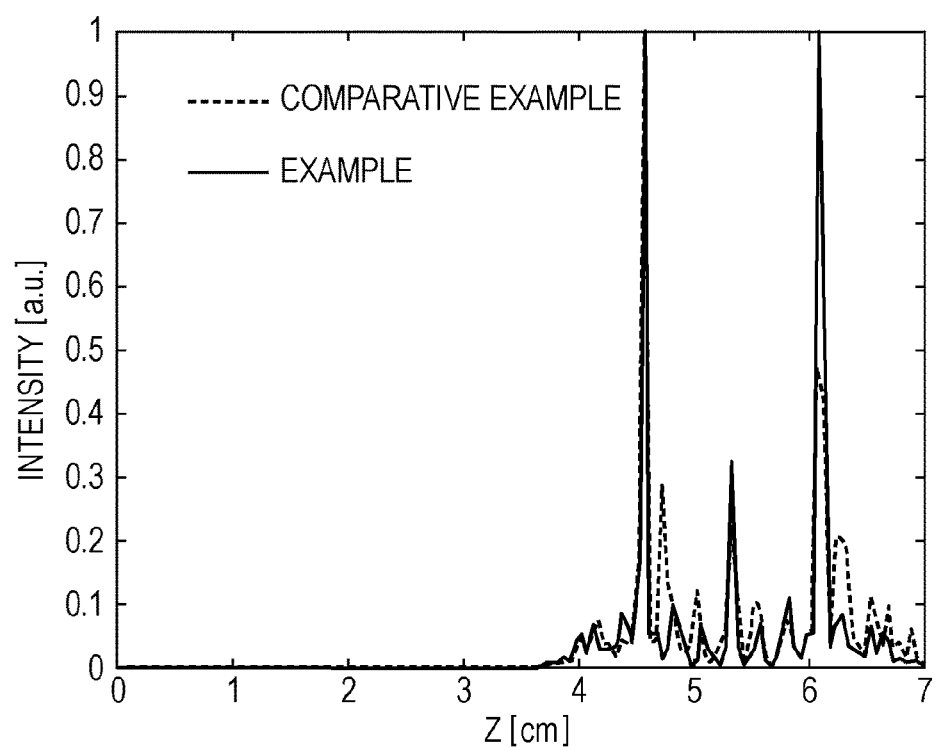
FIG. 9 illustrates the results in FIGS. 7 and 8 taken along a section at Y=1.0 cm.

Further, FIG. 9 illustrates changes of intensity taken along a section at Y=1.0 cm in each of the results illustrated in FIGS. 7 and 8. In FIG. 9, the horizontal axis indicates a distance in the Z direction, and the vertical axis indicates intensity. Moreover, a dotted line represents the result of COMPARATIVE EXAMPLE, and a solid line represents the result of EXAMPLE. Those results in FIG. 9 are each normalized on the basis of a peak appearing near Z=4.5 cm. As seen from those results, the intensities of the artifacts appearing after large peaks, which represent respectively the actual image and the reflected image, are reduced to a background level. Hence, the artifacts can be effectively reduced.

According to the present invention, highly-reliable image data can be obtained by executing the processing to distinguish or reduce the artifact.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Application No. PCT/JP2009/071062, filed Dec. 17, 2009, which is hereby incorporated by reference herein in its entirety.

REFERENCE SIGNS LIST

1 light source
2 light 3 specimen
4 optical component
5 light absorber or initial pressure distribution
6 acoustic wave
7 acoustic wave reflecting plate
8 acoustic wave receiver
9 electrical signal processing circuit
10 image forming apparatus
11 display apparatus
12 scanning controller
14 actual image of light absorber
15 artifact of actual image
16 acoustic wave reflecting surface
17 reflected image of light absorber
18 artifact of reflected image
19 image of acoustic wave reflecting surface
101 volume data producing unit
102 symmetry determining unit
103 tag attaching unit
104 processing unit
105 folded-data producing unit
106 superimposing unit

The invention claimed is:

1. A measuring system comprising:
an acoustic wave receiver for receiving acoustic waves which are generated by irradiating light to a specimen, and for converting the received acoustic waves into an electrical signal; and
an image forming apparatus for producing image data by using the electrical signal,
wherein the acoustic wave receiver receives direct waves and reflected waves in acoustic waves generated from a detection target inside the specimen and coverts the direct waves and the reflected waves into respective electric signals, the direct waves directly reach the acoustic wave receiver, and the reflected waves are reflected by an acoustic wave reflecting surface formed by an interface between the specimen and a medium adjacent to the specimen,
the image forming apparatus includes a central processing unit (CPU) comprising:
a data producing unit for producing image data by converting the electrical signal converted from the direct waves and the electrical signal converted from the reflected waves to voxel data or pixel data;
a determining unit for determining whether, as viewed on the image data, a position of the voxel data or the pixel data converted from the direct waves and a position of the voxel data or the pixel data converted from the reflected waves are symmetrical with respect to the acoustic wave reflecting surface; and
a processing unit for executing a reduction process for images of the voxel data or the pixel data, which are determined to be not symmetrical by the determining unit.

2. The measuring system according to claim 1, further comprising an electrical signal processing circuit for converting the electrical signal, which has been converted by the acoustic wave receiver, to a digital signal,
wherein the data producing unit converts the digital signal to voxel data or pixel data.

3. The measuring system according to claim 1, wherein when the acoustic wave reflecting surface is a curved surface, the data producing unit produces the image data after executing a coordinate transform of the position of the voxel data or the pixel data converted from the reflected waves to a position of the voxel data or the pixel data, which is to be obtained when the acoustic wave reflecting surface is a flat surface.

4. A measuring system comprising:
an acoustic wave receiver for receiving acoustic waves which are generated by irradiating light to a specimen, and for converting the received acoustic waves to an electrical signal; and
an image forming apparatus for producing image data by using the electrical signal,
wherein the acoustic wave receiver receives direct waves and reflected waves in acoustic waves generated from a detection target inside the specimen and coverts the direct waves and reflected waves to respective electrical signals, the direct waves directly reach the acoustic wave receiver, and the reflected waves are reflected by an acoustic wave reflecting surface formed by an interface between the specimen and a medium adjacent to the specimen,
the image forming apparatus includes a central processing unit (CPU) comprising:
a data producing unit for producing image data by converting the electrical signal converted from the direct waves and the electrical signal converted from the reflected waves to voxel data or pixel data;
a folded-data producing unit for folding the image data at a position corresponding to the acoustic wave reflecting surface on the image data, thereby producing folded data; and
a superimposing unit for superimposing the folded data with the image data before being folded.

5. The measuring system according to claim 4, further comprising an electrical signal processing circuit for converting the electrical signal, which has been converted by the acoustic wave receiver, to a digital signal,
wherein the data producing unit converts the digital signal to voxel data or pixel data.

6. The measuring system according to claim 4, wherein when the acoustic wave reflecting surface is a curved surface, the data producing unit produces the image data after executing coordinate transform of the position of the voxel data or the pixel data converted from the reflected waves to a position of the voxel data or the pixel data, which is to be obtained when the acoustic wave reflecting surface is a flat surface.

7. A measuring system comprising:
an acoustic wave receiver for receiving acoustic waves which are generated by irradiating light to a specimen, and for converting the received acoustic waves into an electrical signal; and
an image forming apparatus for producing image data by using the electrical signal,
wherein the acoustic wave receiver receives direct waves and reflected waves in acoustic waves generated from a detection target inside the specimen and coverts the direct waves and the reflected waves to respective electric signals, the direct waves directly reach the acoustic wave receiver, and the reflected waves are reflected by an acoustic wave reflecting surface formed by an interface between the specimen and a medium adjacent to the specimen,
the image forming apparatus including a central processing unit (CPU) comprising:
a data producing unit for producing image data by converting the electrical signal converted from the direct waves and the electrical signal converted from the reflected waves to voxel data or pixel data;
a determining unit for determining whether, as viewed on the image data, a position of the voxel data or the pixel data converted from the direct waves and a position of the voxel data or the pixel data converted from the reflected waves are symmetrical with respect to the acoustic wave reflecting surface; and a processing unit for executing a distinction process for images of the voxel data or the pixel data, which are determined to be not symmetrical by the determining unit.

8. The measuring system according to claim 7, wherein the processing unit executes coloring for the images of the voxel data or the pixel data, which are determined to be not symmetrical by the determining unit, as the distinction process.

9. The measuring system according to claim 7, further comprising an electrical signal processing circuit for converting the electrical signal, which has been converted by the acoustic wave receiver, to a digital signal, wherein the data producing unit converts the digital signal to voxel data or pixel data.

10. The measuring system according to claim 7, wherein when the acoustic wave reflecting surface is a curved surface, the data producing unit produces the image data after executing a coordinate transform of the position of the voxel data or the pixel data converted from the reflected waves to a position of the voxel data or the pixel data, which is to be obtained when the acoustic wave reflecting surface is a flat surface.

11. The measuring system according to claim 7, wherein the processing unit cause a display apparatus to display the images of the voxel data or the pixel data processed using the distinction process.

* * * * *